(12) United States Patent
Dudek et al.

(10) Patent No.: US 8,263,377 B2
(45) Date of Patent: Sep. 11, 2012

(54) LABEL FREE KINASE ASSAYS AND REAGENTS

(75) Inventors: Ronald P Dudek, Sammamish, WA (US); Michael Cicirelli, Kirkland, WA (US); Timothy C Parker, Bothell, WA (US)

(73) Assignee: Plexera, LLC, Woodinville, WA (US)

( * ) Notice: Subject to any disclaimer, the term of this patent is extended or adjusted under 35 U.S.C. 154(b) by 1197 days.

(21) Appl. No.: 12/061,175

(22) Filed: Apr. 2, 2008

(65) Prior Publication Data

US 2012/0157328 A1 Jun. 21, 2012

Related U.S. Application Data

(60) Provisional application No. 60/909,885, filed on Apr. 3, 2007.

(51) Int. Cl.
*C12N 9/12* (2006.01)
*G01N 21/55* (2006.01)

(52) U.S. Cl. ........................... 435/194; 356/445

(58) Field of Classification Search .................. 435/194; 356/244, 445
See application file for complete search history.

(56) References Cited

U.S. PATENT DOCUMENTS

| | | | |
|---|---|---|---|
| 5,536,822 A | 7/1996 | Haystead | |
| 6,165,335 A | 12/2000 | Lennox et al. | |
| 6,461,490 B1 | 10/2002 | Lennox et al. | |
| 6,478,939 B1 | 11/2002 | Lennox et al. | |
| 6,862,094 B2 | 3/2005 | Johansen | |
| 6,999,175 B2 | 2/2006 | Ivarsson | |
| 7,084,980 B2 | 8/2006 | Jones et al. | |
| 7,251,085 B2 | 7/2007 | Bahatt et al. | |
| 7,373,255 B2 * | 5/2008 | Karlsson et al. | 702/19 |
| 7,463,358 B2 | 12/2008 | Wolf et al. | |
| 2004/0258832 A1 | 12/2004 | Barklund et al. | |
| 2005/0014179 A1 | 1/2005 | Karlsson et al. | |
| 2005/0200845 A1 | 9/2005 | Nabatova-Gabain et al. | |
| 2006/0134669 A1 | 6/2006 | Casasanta | |
| 2006/0154320 A1 | 7/2006 | Zuk et al. | |
| 2006/0234265 A1 | 10/2006 | Richey et al. | |
| 2007/0081163 A1 | 4/2007 | Liang et al. | |
| 2007/0128455 A1 | 6/2007 | Wolf | |
| 2007/0139653 A1 | 6/2007 | Guan | |
| 2007/0222996 A1 | 9/2007 | Guan et al. | |
| 2009/0060786 A1 | 3/2009 | Kim et al. | |
| 2009/0060787 A1 | 3/2009 | Kim et al. | |

OTHER PUBLICATIONS

Bogoyevitch et al., "Peptide inhibitors of protein kinases—discovery, characterisation and use," *Biochim. Biophys. Acta*, 2005, 1754:79-99.
Hines et al., "Bisubstrate analog probes for the insulin receptor protein tyrosine kinase: Molecular yardsticks for analyzing catalytic mechanism and inhibitor design," *Bioorg. Chem.*, 2005, 33:285-297.
Komatsu et al., "SPR sensor signal amplification based on dye-doped polymer particles," *Sci. Tech. Adv. Mater.*, 2006, 7:150-155.
Mitchell et al., "Sensitivity enhancement of surface plasmon resonance biosensing of small molecules," *Anal. Biochem.*, 2005, 343:125-135.
Qi et al., "Determination of the Bioavailability of Biotin Conjugated onto Shell Cross-Linked (SCK) Nanoparticles," *J. Am. Chem. Soc.*, 2004, 126(21):6599-6607.
Severs and Schasfoort, "Enhanced surface Plasmon resonance inhibition test (ESPRIT) using latex particles," *Biosens. Bioelectron.*, 1993, 8:365-370.
Shen et al., "Protein kinase structure and function analysis with chemical tools," *Biochim. Biophys. Acta*, 2005, 1754:65-78.
Wink et al., "Liposome-Mediated Enhancement of the Sensitivity in Immunoassays of Proteins and Peptides in Surface Plasmon Resonance Spectrometry," *Anal. Chem.*, 1998, 70:827-832.
Kim et al.; U.S. Appl. No. 12/339,017, filed Dec. 18, 2008.

* cited by examiner

*Primary Examiner* — Chih-Min Kam
(74) *Attorney, Agent, or Firm* — Sci-Law Strategies, PC

(57) ABSTRACT

This disclosure describes methods and compositions for measuring the binding specificity, kinetics and affinity of kinase inhibitors indirectly using mass sensing analytical techniques, such as SPR, through the competitive displacement of detectable signal-inducing kinase binding molecule. Further provided are methods for preparing such molecules.

12 Claims, 3 Drawing Sheets

LABEL FREE KINASE ASSAYS AND REAGENTS

CROSS-REFERENCE TO RELATED APPLICATIONS

This application claims priority benefit from and incorporates by reference U.S. Provisional Patent Application Ser. No. 60/909,885; entitled LABEL FREE KINASE ASSAYS AND REAGENTS; invented by Ronald P. Dudek, et al.; and filed on Apr. 3, 2007.

TECHNICAL FIELD

This disclosure relates to the preparation of detectable kinase binding molecules and assays involving ATP utilizing biomolecules, including kits and methods of use thereof.

BACKGROUND

Several classes of molecules possess a structural pocket for the binding of adenosine triphosphate (ATP). Molecules that include a structural pocket for binding ATP include enzymes such as kinases, ATP binding cassette transporters, and myosin. ATP serves as an energy source for the catalysis of reactions through the cleavage of a high energy phosphate bond.

Protein kinases typically bind ATP in a binding pocket that resides in a structurally conserved catalytic domain. ATP binding, in conjunction with the inherent ability of protein kinases to bind small organic molecules, has made the ATP binding site of protein kinases a target of many small molecule protein kinase inhibitor drug discovery efforts. Several technologies have been developed to allow for the screening of protein kinase inhibitors. Many measure the inhibition of phosphorylation of a substrate by a protein kinase in the presence of a potential kinase inhibitor as the means of screening. While these technologies provide a read-out of kinase inhibition from a functional perspective, they may not measure binding and may provide little or no kinetic information.

SUMMARY

Kinase inhibitor drug compounds are typically small molecule organic compounds of 200-500 Dalton. Detection of the binding of such small molecules to larger protein kinases can challenge the detection sensitivity limits of analytical platforms that rely on molecular mass or size, such as surface plasmon resonance (SPR) (including grating coupled SPR and Kretschmann prism coupling SPR), acoustic resonant biosensors, mass spectrometry, and "bio-layer" interferometry (for example see U.S. Patent Publication No. 2006/0154320). This disclosure describes a solution for measuring the binding specificity, kinetics, and affinity of small molecules that bind kinases, such as kinase inhibitors, indirectly through the competitive displacement of a kinase binding molecule (KBM) that is attached to a signal-inducing group (SG). The KBM may include, for example, Adenosine triphosphate (ATP) derivatives, ATP analogs, ATP mimetics, and small molecule kinase inhibitors that bind the active site of kinases (e.g., staurosporine). The KBM may also include a molecule that binds to another part of the kinase, for example, a regulatory subunit (e.g., the binding sites of A-kinase anchoring proteins).

According to an embodiment, the signal-inducing group may include a chemical group that provides a detectable signal above the noise level in an analytical instrument, such as an instrument that uses a mass-based detection system. In contrast, the KBM alone may not provide a detectable signal above the noise level in the same analytical instrument.

Typically, the SG increases the molecular mass of the KBM from 3 to 5000 times. Non-limiting examples of analytical instruments that use mass-based detection systems include SPR biosensors, acoustic resonant biosensors, mass spectrometers, or bio-layer interferometers. In certain embodiments, an SG is covalently bound to a KBM though a linker (L). Displacement of the signal-inducing KBM by a kinase inhibitor drug candidate may result in a signal change in a biosensor that relies on mass or size for detection.

A variety of such signal-inducing KBMs may be prepared. These compounds can have the general formula:

where SG is a signal inducing group; L is a linker; KBM is a kinase binding molecule; m is an integer from 1 to 5; and n is an integer from 0 to 5. In specific embodiments, m is 1. In other embodiments, n is 0 or 1.

In some embodiments, [SG] is selected from the group consisting of a polypeptide, metal nanoparticle, polymer particle, and liposome. In certain instances, when the SG is a polypeptide, it can have a mass of up to about 3000 kDa.

In other embodiments, [KBM] is selected from the group consisting of ATP; ATP-γ-S; 6-Bn-ATP; 6-(3MeBn)-ATP; 6-(1MeBu)-ATP; 6-(2MeBu)-ATP; 6-Phe-ATP; adeonosine-5-(γ-4-aminophenyl)triphosphate; β,γ-CH$_2$-adenosine-5-triphosphate; P[NH]ppA; AMP-PNP; AMP-PCP; ε-ATP; dATP; adenosine tetraphosphate; ADP; AMP; AMP-PCH[2]P,3; biotinyl-ATP; and AMP-PCA[s].

In another embodiment, [L] is selected from the group consisting of complexed biotin; 1,6-diaminohexane; γ-aminophenyl(CH$_2$)$_p$; γ-aminooctyl(CH$_2$)$_p$; γ-aminohexyl(CH$_2$)$_p$; —S(PEG)$_q$CO$_2$NHS—; —S(CH$_2$)$_p$(PEG)$_q$(CH$_2$)$_p$OCOCH$_2$S—; —S(CH$_2$)$_p$NHCO(CH$_2$)$_r$CONH—; —CO$_2$NH—; —S(CH$_2$)$_p$NHCOCH$_2$S—; —CONH(CH$_2$)$_p$(PEG)$_q$(CH$_2$)$_r$COCH$_2$S—; where p and r are independently integers from 0 to 20 and q is an integer from 0 to 100. In certain instances, [L] is selected from the group consisting of: γ-aminophenyl(CH$_2$)$_{10}$, γ-aminooctyl(CH$_2$)$_8$; γ-aminohexyl(CH$_2$)$_6$; —S(CH$_2$)$_2$(PEG)$_q$(CH$_2$)$_2$OCOCH$_2$S—; —S(CH$_2$)$_3$NHCO(CH$_2$)$_3$CONH—; —S(CH$_2$)$_6$NHCOCH$_2$S—; and —CONH(CH$_2$)$_2$(PEG)$_q$(CH$_2$)$_2$COCH$_2$S—. In further instances, [L] is selected from the group consisting of:

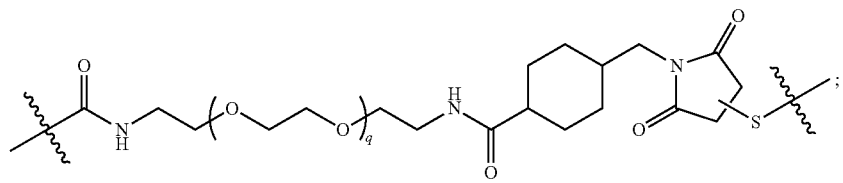

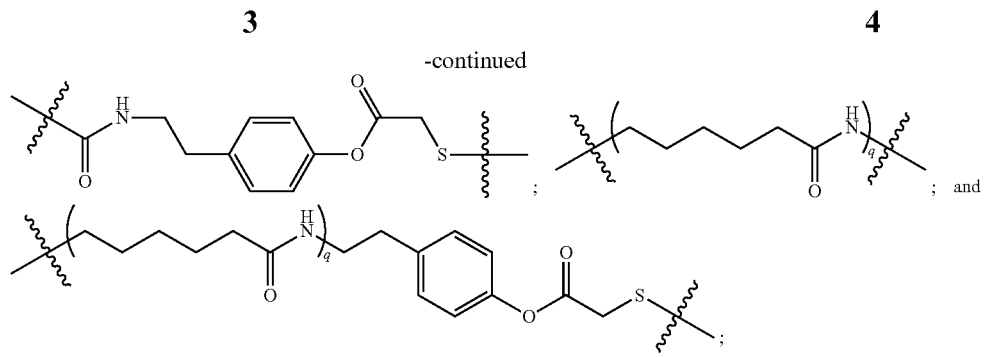

wherein q is an integer from 1 to 100.

In some embodiments, a biotin complex may be selected from avidin-biotin, streptavidin-biotin, and neutrastreptavidin-biotin.

In further embodiments, a composition containing a signal-inducing KBM may also include a kinase inhibitor candidate, a known kinase inhibitor, or both. In another embodiment, a signal-inducing KBM may form part of a kit. The kit may include a signal-inducing KBM and a kinase SPR array. In some instances, the kit may also include a known kinase inhibitor. The known kinase inhibitor may be specific to the kinase of the SPR array.

When the KBM has a moiety that mimics ATP, the KBM may be used to probe arrays of biomolecules, proteins, or enzymes that utilize ATP. In this case, the signal-inducing KBM can be defined as a signal-inducing ATP mimic (ATPM). The signal-inducing ATPM may be used in assays involving other biomolecules, proteins, or enzymes that utilize ATP, for example mysosin and ATP binding cassette transporters. Thus, another embodiment may include using a signal-inducing ATP mimic to probe arrays of ATP utilizing molecules. The array of ATP utilizing molecules may include biomolecules, proteins, enzymes, or any combination thereof. In one embodiment, the signal-inducing ATP mimic may be immobilized on the surface of a microarray. The microarray may then be probed with at least one ATP utilizing molecule. In another embodiment, an assay may include introducing an analyte (e.g., a small molecule drug candidate) to a myosin array loaded with signal-inducing KBMs and detecting a change in the SPR signal when the analyte displaces the signal-inducing KBMs.

A signal-inducing KBM may be prepared through the attachment of additional molecules. One example of a signal-inducing KBM is a biotinylated ATP that has been linked to streptavidin. The molecular weight of the resulting complex is approximately 60,000 Daltons, a relatively large molecule whose binding and displacement are within the detection limits of analytical platforms like SPR. Use of this signal-inducing KBM can include loading arrayed protein kinases with a signal-inducing KBM, and screening inhibitor candidates over this loaded array. Measurement of the displacement of the signal-inducing KBM from individual protein kinases by kinase inhibitors may be utilized to derive binding specificity, kinetics, and affinity data for the kinase inhibitors.

Also provided herein is a method for characterizing a kinase inhibitor candidate. In certain embodiments, this method may include contacting the candidate with a kinase SPR array and characterizing the candidate based on the interaction between the inhibitor candidate and the array. In some instances, the method may include: a) providing a kinase inhibitor candidate; b) providing a signal-inducing KBM; and c) contacting the kinase inhibitor candidate and the signal-inducing KBM with a kinase SPR array.

In some embodiments, the inhibitor candidate is contacted with the SPR array before the signal-inducing KBM. In such a case, the signal-inducing KBM may be prevented from reaching as high an SPR signal and/or may reach a given SPR signal more slowly (e.g., may have a lower apparent association rate constant), compared to when the inhibitor candidate is not contacted with the SPR array prior to the signal-inducing KBM. This is because the inhibitor candidate may block the binding pockets of the immobilized protein kinases to which the signal-inducing KBM may bind. Thus a lower signal-inducing KBM association constant and/or a lower signal-inducing KBM equilibrium constant may indicate a relatively higher kinase affinity (and higher affinity constant and/or higher equilibrium constant) by the kinase inhibitor candidate.

In other embodiments, the inhibitor candidate is contacted with the SPR array after the signal-inducing KBM. In such embodiments, the apparent dissociation constant of the signal-inducing KBM may be increased (indicating a higher apparent rate of dissociation) owing to competitive binding in the binding pockets by the inhibitor candidate, which may prevent re-binding by recently dissociated signal-inducing KBM molecules. Thus a relatively higher apparent dissociation constant for the signal-inducing KBM may indicate a relatively higher association constant for the kinase inhibitor candidate.

In another embodiment, the inhibitor candidate and the signal-inducing KBM are contacted with the SPR array substantially simultaneously. This may result in a lower apparent association constant for the signal-inducing KBM, owing to competition for the protein kinase binding pockets by the kinase inhibitor candidate. The equilibrium constant for the signal-inducing KBM may be similarly reduced, owing to partial filling of kinase binding pockets by the kinase inhibitor candidate. A relatively lower the signal-inducing KBM association constant and binding equilibrium constant may indicate higher affinity for the binding pockets by the kinase inhibitor candidate.

Another aspect is the validation of the functionality of arrayed protein kinases. One current shortcoming of protein arrays is the inability to determine if the arrayed protein is representative structurally and functionally of the protein in vivo. By determining if a signal-inducing KBM, which is capable of binding to the ATP binding domain, binds to the individual arrayed protein kinases, a validation of the relevant functionality of the protein kinases can be observed, that is, a functional ATP binding pocket may be demonstrated.

In certain embodiments, validation of the functionality of an arrayed protein kinase may include contacting the SPR-arrayed kinase with a signal-inducing KBM, and characterizing the SPR-arrayed kinase based on the interaction between the SPR-arrayed kinase and the signal-inducing KBM.

Another aspect of this disclosure includes a method for differentiating in-ATP-pocket binding versus out-of-ATP-pocket binding (i.e., allosteric binding) of molecules, such as protein kinase inhibitors.

The details of one or more embodiments are set forth in the accompanying drawings and the description below. Other features, objects, and advantages of the invention will be apparent from the description and drawings, and from the claims.

DETAILED DESCRIPTION

Figure 1:
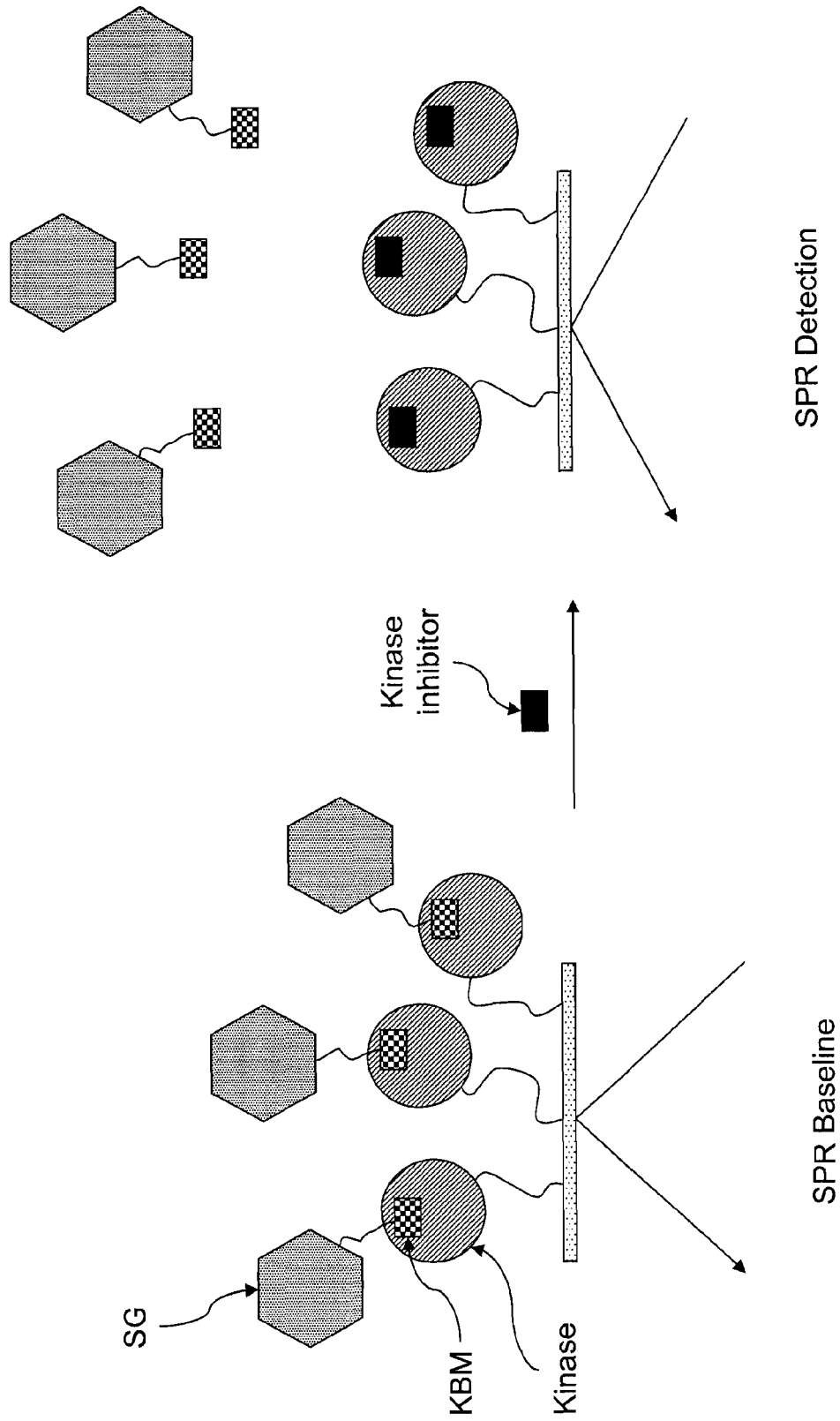
FIG. 1 illustrates a first embodiment of a displacement assay.

This disclosure describes methods and compositions for measuring the binding specificity, kinetics, and affinity of kinase inhibitor candidates indirectly, through the competitive displacement of detectable KBMs.

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there is a plurality of definitions for a term herein, those in this section prevail unless stated otherwise.

Design of Signal-inducing, Detectable KBMs

Provided herein are signal-inducing KBMs that are useful for the detection and quantification of protein kinase inhibitor molecule binding by analytical methods such as SPR. These signal-inducing KBMs may be used to overcome the detection sensitivity limits of analytical instruments by increasing the mass or size of the KBM through the addition of a signal-inducing group (SG). For example, a KBM may be modified to include an SG that is an SPR Enhancing Moiety. A KBM may be optionally linked with an SG though a linker (L). A variety of such signal-inducing KBMs can be prepared. These compounds can have a general formula:

[SG]$_m$–[L]$_n$–[KBM], where m is an integer from 1 to 5. and n is an integer from 0 to 5.

Examples of signal-inducing KBMs may include the following:

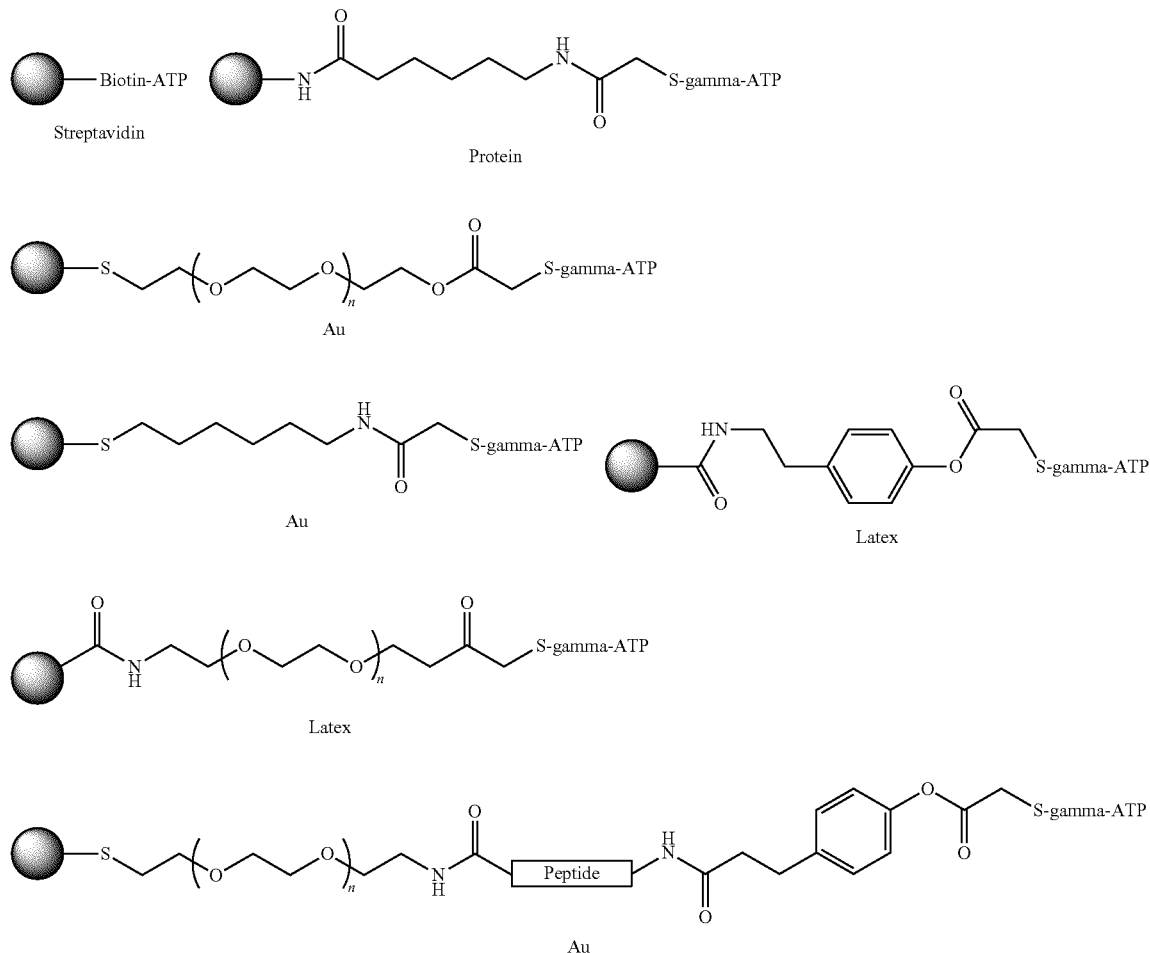

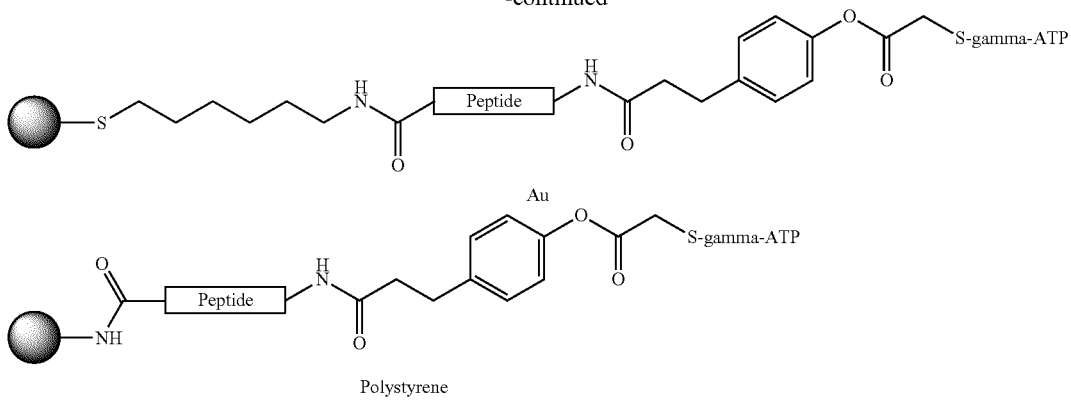

Kinase Binding Molecule

A KBM may include any suitable molecule that is able to bind to a protein kinase in a binding domain (e.g., ATP binding domain, regulatory subunit, substrate binding domain, allosteric site, or other catalytic site). Non-limiting examples of KBMs are shown in Table I.

TABLE I

Examples of Kinase Binding Molecules.

| Abbreviation | Name |
| --- | --- |
| ATP | adenosine triphosphate |
| ATP-γ-S | adenosine-5'-O-(3-thiotriphosphate) |
| 6-Bn-ATP | $\eta^6$-benzyladenosine-5'-triphosphate |
| 6-(3MeBn)-ATP | $\eta^6$-(3-methylbenzyl)adenosine-5'-O-triphosphate |
| 6-(1MeBu)-ATP | $\eta^6$-(1-methylbutyl)adenosine-5'-O-triphosphate |
| 6-(2MeBu)-ATP | $\eta^6$-(2-methylbutyl)adenosine-5'-O-triphosphate |
| 6-Phe—ATP | $\eta^6$-phenyladenosine-5'-O-triphosphate |
| | adenosine-5-(γ-4-aminophenyl)triphosphate |
| P[NH]ppA | adenosine-5'-(β,γ-imido)triphosphate |
| | adenosine-5'-(β,γ-methylene)triphosphate |
| AMP-PNP | adenyl-5'-yl imidodiphosphate |
| AMP-PCP | adenosine-5'-(β,γ-imido)triphosphate |
| ε-ATP | 1-$\eta^6$-ethenoadenosine-5'-triphosphate |
| dATP | deoxyadenosine triphosphate |
| | adenosine tetraphosphate |
| ADP | adenosine diphosphate |
| AMP | adenosine monophosphate |
| AMP-PCF[2]P,3 | β,γ-difluoromethyleneadenosine-5'-triphosphate |
| biotinyl-ATP | biotinylated adenosine triphosphate |
| AMP-PCA[s] | γ-arsono-β,γ-methylene adenosine-5'-triphosphate |

The KBM may also comprise a pseudosubstrate that binds to the catalytic site of the kinase, for example, see, M. A. Bogoyevitch et al., Biochim. Biophys. Acta, 1754, 79-99 (2005). Such pseudosubstrates are typically enzyme dependent and may include polypeptides or small molecule inhibitors. Examples of polypeptides for particular enzymes may include, R-F-A-R-K-G-A-L-R-Q-K-N-V-H-E-V-K-N (SEQ ID NO:1), R-F-A-R-K-G-A-L-R-Q-K-N-V (SEQ ID NO:2), and MryF-A-R-K-G-A-L-R-Q (SEQ ID NO:3) for kinase PKCα/β/γ, and MryFR-R-G-A-R-R-W-R-K for PKC-ζ(SEQ ID NO:4). Small molecule inhibitors may include such compounds as staurosporine, imantinib mesylate (Gleevec®), sunitinib malate (Sutent®), and sorafenib tosylate (Nexavar®).

Signal-inducing Group (SG)

A signal-inducing group can be any chemical group that provides a signal substantially above the noise level in an analytical instrument that uses a mass-based detection system, where the KBM alone would not provide a signal substantially above the noise level in the same analytical instrument. Typically, the SG adds to the molecular mass of the KBM from 3 to 5000 times that of the KBM alone (e.g., 3 to 4000 times, 3 to 3000 times, 3 to 2000 times, 3 to 1000 times, 10 to 5000 times, 100 to 5000 times, 500 to 5000 times, 1000 to 5000 times, 5 to 100 times, 100 to 1000 times, 250 to 4000 times, 500 to 2500 times, and 1000 to 3000 times). Non-limiting examples of analytical instruments that use mass-based detection systems include SPR biosensors, acoustic resonant biosensors, mass spectrometers, and bio-layer interferometers.

Non-limiting examples of SGs include polypeptides (e.g., proteins), oligonucleotides, carbohydrates, lipids, and nanoparticles, including metal nanoparticles (e.g., gold nanoparticles see: J. S. Mitchell, et al., Anal. Biochem. 343, 125-135 (2005)), polymer nanoparticles (e.g., latex particles see: A. H. Severs, et al., Biosens. Bioelectron. 8, 365-370 (1993) and H. Komatsu, et al., Sci. Tech. Adv. Mater 7, 150-155 (2006)), liposomes (e.g., T. Wink, et al., Anal. Chem. 70, 827-832 (1998)), and glass/SiOx nanoparticles.

A polypeptide may be a length that is sufficient to be detected by methods such as, for example, SPR. For example, the molecular weight of a polypeptide may be at least approximately 10 times that of the KBM (e.g., if the KBM has a MW ~600. then a corresponding polypeptide SG may have a MW of ~6000). The composition of such polypeptides may vary depending on the molecular weight of the constituent amino acids (e.g., polypeptides rich in lighter Gly (MW=75), Ala (MW=89), and/or Ser (MW=105) amino acids may comprise at least 80 residues, while polypeptides rich in heavier Trp (MW=204), Tyr (MW=181), and/or Arg (MW=174) amino acids may comprise at least 30 residues. The polypeptides may also be proteins such as avidin/streptavidin.

A nanoparticle can be a metal nanoparticle, for example a gold, silver, copper, and nickel nanoparticle, or other nanoparticle such as silicon dioxide ($SiO_2$) nanoparticle.

A polymer particle can be, for example, a latex particle, a polyphosphate, a poly(ADP-ribose), a DNA, an RNA, or a shell crosslinked nanoparticle, for example, see, K. Qi et al., J. Am. Chem. Soc. 126(21), 6599, 2004.

A liposome can include phospholipid derivatives such as derivatives of phosphoglycerides (e.g., phosphatidyl choline, phosphatidyl ethanolamine, phosphatidyl inositol, phosphatidyl serine, and diphosphatidyl glycerol) and sphingomyelin.

Linker

In some embodiments, an SG is covalently bound to a KBM through a linker (L). The linker may vary in length and may have appreciable mass itself that adds to the molecular mass of the complex. In embodiments where the KBM or SG includes a peptide, the L can cap the N-terminus of the peptide, the C-terminus, or both N- and C-termini, as an amide moiety. Other exemplary capping moieties include sulfonamides, ureas, thioureas and carbamates. L's can also include linear, branched, or cyclic alkanes, alkenes, or alkynes, and phosphodiester moieties. L may be substituted with one or more functional groups, including ketone, ester, amide, ether, carbonate, sulfonamide, or carbamate functionalities.

Further examples of linkers can include complexed biotin (e.g., avidin-biotin, streptavidin-biotin, and neutrastreptavidin-biotin); 1,6-diaminohexane; γ-aminophenyl$(CH_2)_p$; γ-aminooctyl$(CH_2)_p$; γ-aminohexyl$(CH_2)_p$; —S(PEG)$_q$CO$_2$NHS—; —S$(CH_2)_p$(PEG)$_q$$(CH_2)_p$OCOCH$_2$S—; —S$(CH_2)_p$NHCO$(CH_2)_r$CONH—; —CO$_2$NH—; —S$(CH_2)_p$ NHCOCH$_2$S—; —CONH$(CH_2)_p$(PEG)$_q$$(CH_2)_r$COCH$_2$S—; where p and r are independently integers from 0 to 20 (e.g., 2, 3, 4, 6, 8, 10, 12, 16, and 20) and q is an integer from 0 to 100. For example, γ-aminophenyl$(CH_2)_{10}$; γ-aminooctyl$(CH_2)_8$; γ-aminohexyl$(CH_2)_6$; —S$(CH_2)_2$(PEG)$_q$$(CH_2)_2$OCOCH$_2$S—; —S$(CH_2)_3$NHCO$(CH_2)_3$CONH—; —S$(CH_2)_6$NHCOCH$_2$S—; —CONH$(CH_2)_2$(PEG)$_q$$(CH_2)_2$COCH$_2$S—.

Further examples of linkers are as follows:

This linker may include peptides having from about 3 to about 20 amino acids (e.g., about 3 to about 10 amino acids; about 5 to about 15 amino acids; about 8 to about 20 amino acids; and from about 10 to about 16 amino acids). Examples of such peptide components include -Lys-Lys-Lys-Lue-Pro-Ala-Thr-Gly-Asp- (SEQ ID NO:5) and -Met-Asn-Met-Ser-Pro-Val-Gly-Asp- (SEQ ID NO:6).

Methods of Making

As described above, signal-inducing KBMs can be prepared through the attachment of additional molecules to the KBM molecule. KBMs, such as ATP derivatives, can be synthesized by a variety of methods known in the art. The following are non-limiting examples of the preparation of some such derivatives.

In one embodiment, a signal-inducing KBM can be prepared from a biotinylated ATP that has been linked to streptavidin. The molecular weight of the resulting complex is approximately 60,000 Dalton, a relatively large molecule whose displacement is within the detection limits of analytical platforms like SPR.

As described above, an ATP derivative can be prepared through the attachment of an SG to a KBM (see Scheme I). In one embodiment, an SG moiety can be linked to biotinyl-ATP via avidin, streptavidin, neutrastreptavidin, or the like. For

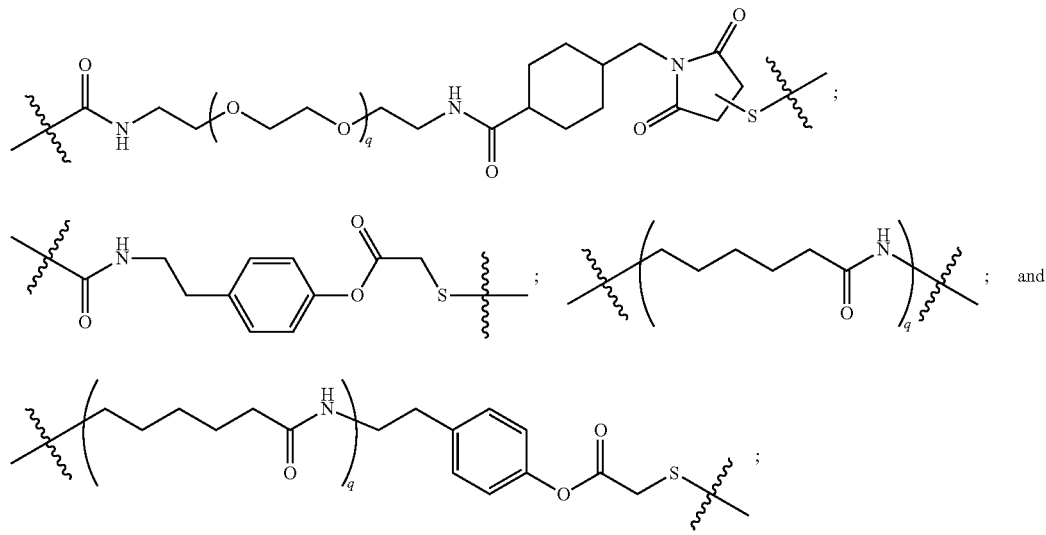

wherein q is an integer from 0 to 100.

In some embodiments, the linker may be capable of binding to the peptide binding region of a kinase active site (i.e., some or all of the linker may be considered part of the KBM). One example of such a linker has the following general structure (see A. C. Hines et al., Bioorg. Chem. 33, 285-297 (2005):

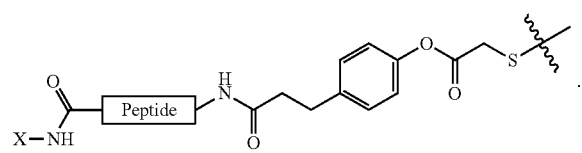

example, avidin can be covalently bound, (e.g., crosslinked) to a metal nanoparticle using bifunctional crosslinking agents, such as HS-PEG-CO$_2$NHS for gold nanoparticle-avidin primary amine coupling. Methods of coupling a polymer or latex particle and avidin can include direct coupling of the primary amine groups of avidin to the carboxy groups of a latex particle facilitated by water soluble carbodiimides. Metal nanoparticles or polymer particles also can be conjugated to biotin, complexed with avidin, and then complexed with biotinyl-ATP. The thiol groups of avidin also can be used in crosslinking. Liposomes can be crosslinked to avidin using N-((4-maleimidylmethyl) cyclohexane-1-carbonyl)-1,2-dihexadecanoyl-sn-glycero-3- phosphoethanolamine, triethylammonium salt (MMCC DHPE).

Scheme I

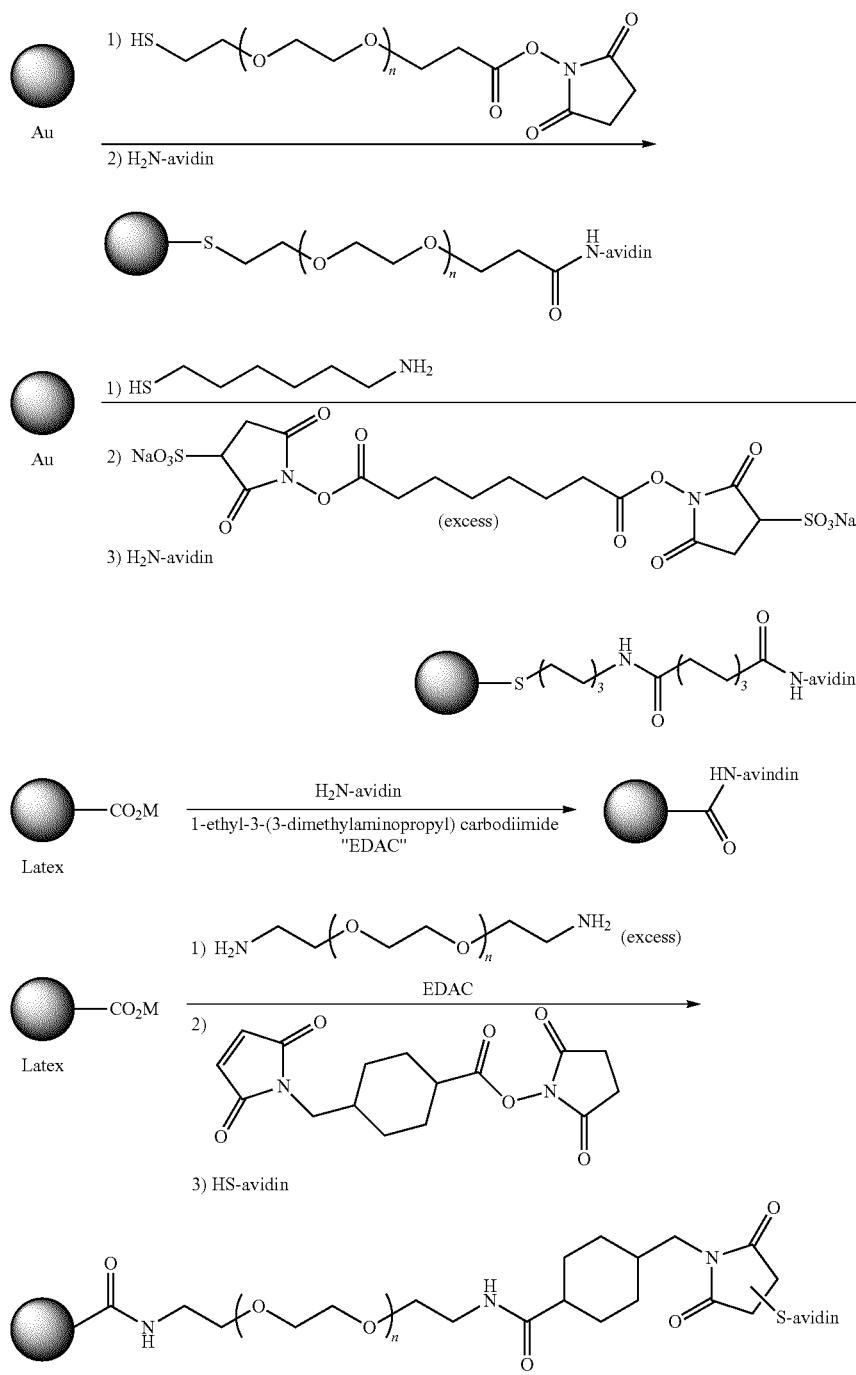

An SG can also be linked to ATP (to form an ATP derivative KBM) at the gamma-phosphate position via a variety of methods (see Scheme II). For example, ATP-γ-S can be reacted with a variety of functional groups to form a chemical bond (e.g., see, A. C. Hines, et al., *Bioorg. Chem.* 33, 285-297 (2005)). Functional groups can include alkyl halides, alkyl bromo esters, 5-dithio-(2-nitrobenzoic acid), or a maleimide. The functional groups may be part of a bifunctional molecule or a part of a larger molecule including a polypeptide or a polymer. A polyethylene glycol (PEG) spacer also may be used to link an SG with a KBM using any one of the variety of bifunctional PEG reagents that are known. For example, when the KBM is an ATP derivative, (see Scheme II), an HS-PEG-OH may be reacted with gold nanoparticles, bromoacetyl bromide, and ATP-γ-S to give nanoparticle-S-PEG-O—(CO)CH$_2$—S-γ-ATP. Another example can include reacting the carboxy groups of a latex particle with an amine-hydroxy bifunctional linker compound and a carbodiimide coupling agent, bromoacetyl bromide, and ATP-γ-S to give latex-amide-linker-O—(CO)—CH$_2$—S-γ-ATP. ATP derivatives also may be prepared from adenosine polyphosphates as in U.S. Pat. No. 5,536,822.

Scheme II

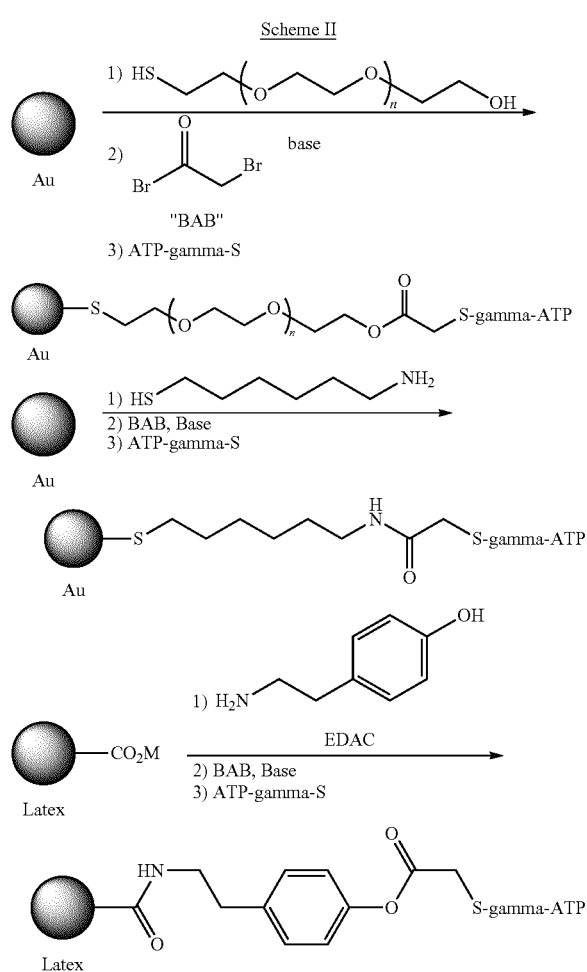

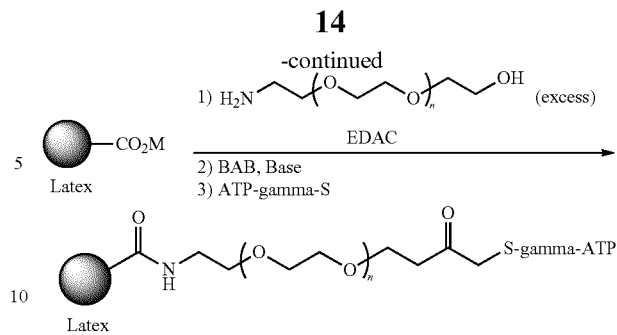

Typically, the catalytic sites of kinases bind both small peptide fragments of the proteins they phosphorylate and ATP; for example, see, K. Shen, et al., *Biochim. Biophys. Acta*, 1754, 65-78 (2005). There may be an organic linker group between the peptide and the KBM to mimic either associative or dissociative transition states. Thus, the linker for the SG can include a peptide fragment that mimics substrates of the target kinases or binds to the peptide binding area in the catalytic site. Peptides can be synthesized from the surface of the metal nanoparticles or polymer particles or can be attached through a linker (see Scheme III). For example, an HS—PEG-NHFMOC can be reacted with gold nanoparticles and deprotected to produce a gold nanoparticle-S-PEG-NH$_2$ intermediate. This intermediate can be subjected to iterative amino acid-NH—FMOC/deprotection and peptide synthesis to give the gold-nanoparticle-S—PEG-NH-Peptide-NH—FMOC, which can be deprotected and end capped with a carboxylic acid/protected phenol group. The phenol can then be deprotected, reacted with bromoacetyl bromide and ATP-γ-S to give a nanoparticle-S—PEG-NH-Peptide-NH—CO-linker-S-γ-ATP. Alternatively, a peptide can be synthesized separately and coupled to a reactive particle (see Scheme III). For example, an aminated polystyrene can be reacted with HO$_2$C-peptide-NH—FMOC, followed by deprotection, coupling with a bifunctional endcap reagent, and reaction with bromoacetyl bromide and ATP-γ-S to produce Polystyrene-Peptide-Linker-S-γ-ATP.

Scheme III

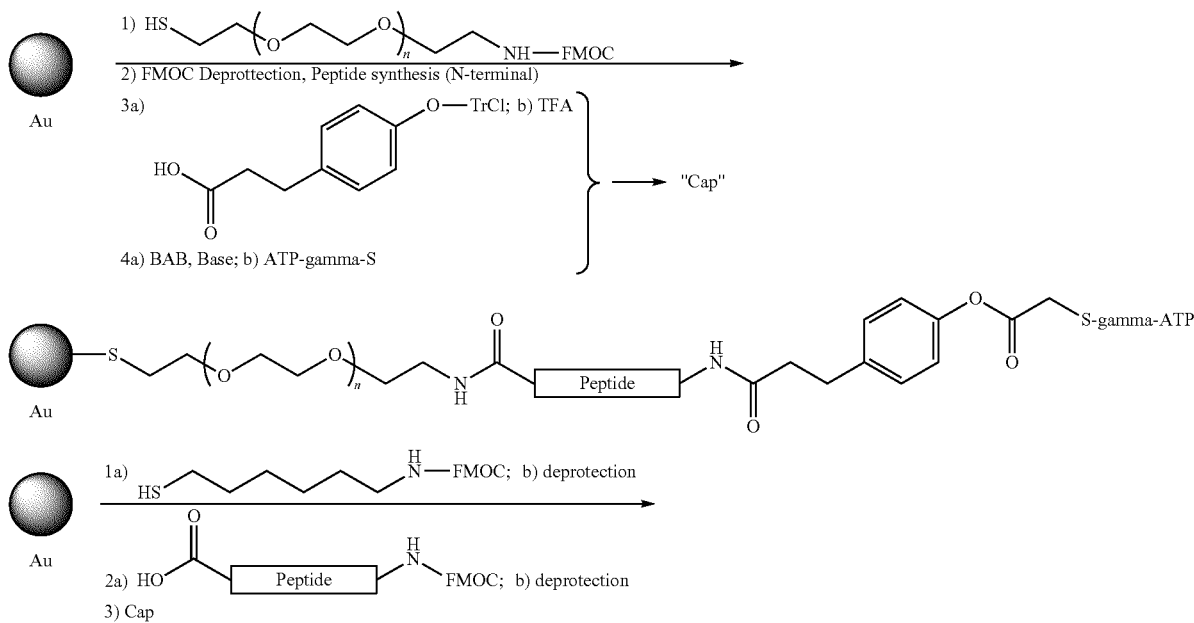

-continued

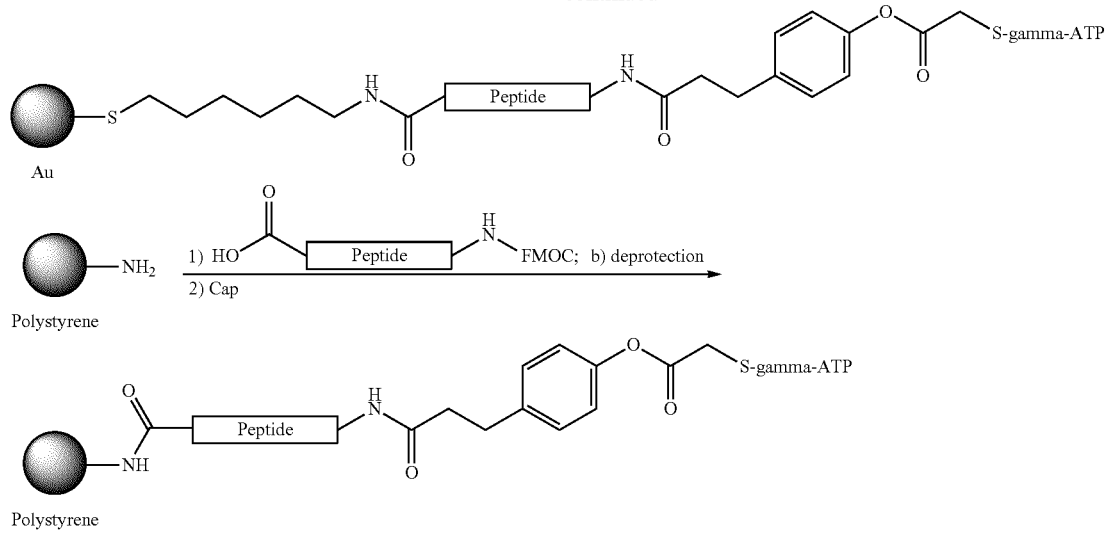

Kinase SPR Arrays

A kinase SPR array may be a structure having one or more immobilized protein kinases that is optically active over a range of wavelengths and that exhibits surface plasmon resonance effects. Such SPR effects can be dependent on the surface characteristics of the array. For example, an SPR array can be composed of a pre-formed surface relief profile using metallised diffraction gratings, metal coated prisms, or a metal film (e.g., silver, gold, copper, aluminum, sodium, indium, copper, titanium, or chromium). In some embodiments, gold may be used. The metal film (e.g., gold) may be coated on a surface (e.g., glass, silicon, or polymeric material) or may compose the surface itself The array format can include, but is not limited to, planar and bead array formats. See, for example, U.S. patent application Ser. No. 11/422/698, entitled "MEMS Micromirror Surface Plasmon Resonance Biosensor and Method," filed Jun. 7, 2006, and Ser. No. 11/296,659, entitled "Highly Stable Surface Plasmon Resonance Plates, Microarrays, and Methods," filed Dec. 6, 2006. and incorporated by reference herein.

Protein kinases may be immobilized onto the surface of an SPR array by a variety of methods known in the art. Immobilization of the kinase may be direct (e.g., covalent coupling to the array surface) or indirect (e.g., through capture of the kinase by a molecule that is covalently coupled to the array surface). When direct immobilization is used, any type of coupling that renders the ligand covalently linked to the metal surface may be used (e.g., linking through amine, thiol, or aldehyde functional groups). In some instances, a self-assembled monolayer (SAM) is used to covalently link the metal film and the kinase. For example, when a gold surface is used, a kinase may be linked through an n-alkanethiol, or a derivative thereof. A SAM can provide a layer to which a kinase may be covalently immobilized using standard amine, thiol, or aldehyde chemistry.

For example, primary amines of the kinase may be directly coupled to a surface coated with carboxyl groups using carbodiimide and N-hydroxysuccinimide. Carboxy covered surfaces are well known in the art and include carboxy-capped monolayers and carboxymethylated dextran covalently linked to an SPR metal. The kinases also can be directionally linked through a fusion tag such as a hexahistidine (His-tag), a coil peptide for a coiled-coil interaction, maltose binding protein, or galactose binding protein. In certain embodiments, kinases can be crosslinked to an amine capped monolayer using hetero- or homo-functional crosslinkers such as bis-NHS crosslinkers or NHS-maleimide crosslinkers. Kinases may also be conjugated to an antigen/hapten or antibody that ligates a respective binding partner that is immobilized on the gold surface. In another embodiment, kinases can also be immobilized by non-covalent binding such as though biotin/avidin interactions, hydrogen bonding, hydrophobic-hydrophobic interactions, or combinations thereof.

A kinase SPR array may be in the form of a microarray. The microarray may include a piece of glass or plastic on which one or more protein kinases have been affixed at separate locations in an ordered manner, thus forming a microscopic array. The kinase SPR array may include a glass slide chip or nano-well array. See, for example, U.S. patent application Ser. No. 11/422/698, entitled "MEMS Micromirror Surface Plasmon Resonance Biosensor and Method," filed Jun. 7, 2006, and Ser. No. 11/296,659, entitled "Highly Stable Surface Plasmon Resonance Plates, Microarrays, and Methods," filed Dec. 6, 2006, incorporated by reference herein.

A protein kinase capable of binding a KBM as described herein may be utilized in a kinase SPR array. For example, Akt/Protein kinase B; Aurora A, B and C protein kinases; B-lymphoid tyrosine kinase (blk); ZAP-70; MAPK-activated protein kinases; kinase insert domain-containing receptor (KDR); members of the stress-activated protein kinase 1 (SAPK) family; JAKs (e.g., JAK1, JAK2, JAK3, Tyk2); interleukin-1 receptor-associated kinase-1 (IRAK1); homeodomain-interacting protein kinase-3 (HIPK3); hematopoietic cell kinase (Hck); and G protein-coupled receptor kinases (GRKs), may be used in a kinase SPR array.

Kits

Kits including one or more of the KBMs described above are also provided. For example, a kit can include a signal-inducing KBM and one or more kinase SPR arrays. The kit can further include positive and negative control kinase inhibitors, for example, known kinase inhibitors that can be specific and non-specific to the protein kinases used in the kinase SPR arrays included in the kit. Optional ingredients in the kits can include instructions for methods of use.

Methods of Use

Provided herein is a method of assaying protein kinase binding. In some instances the binding can be between an immobilized protein kinase and an analyte (e.g., a signal-inducing KBM, a known kinase inhibitor, or a candidate kinase inhibitor). In certain embodiments the analyte may be provided in a fluid sample which is contacted with the kinase SPR array. Contact between the analyte solution and the protein kinase may occur by static or dynamic (e.g., flow cell) means. Protein kinase binding can be observed through monitoring changes in the SPR signal upon binding or release of an analyte from an immobilized kinase.

Suitable assay formats can include any known in the art, for example, competition assays, sandwich assays, agglutination assays, complex precipitation assays, or displacement assays. In certain embodiments, a competition assay can involve competition between two analytes (e.g., a signal-inducing KBM and an inhibitor candidate) for binding to the kinase SPR array. In other embodiments, a displacement assay may be used. For example, displacement of a signal-inducing KBM from the kinase SPR array by an inhibitor candidate may be used. In one embodiment, an assay comprises introducing an analyte (e.g., a kinase inhibitor drug candidate) to a kinase array loaded with a signal-inducing KBM and detecting a change in the SPR signal when the analyte displaces the signal-inducing KBM (see FIG. 1). The measurement of the displacement of the signal-inducing KBM from an individual protein kinase by an inhibitor candidate can be utilized to derive binding specificity, kinetics, and affinity data for the inhibitor candidate. Another embodiment can include creating mixtures of one or more inhibitor candidates and a signal-inducing KBM and analyzing the mixtures using a kinase SPR array for the binding and/or inhibition of binding of the signal-inducing KBM. Alternatively, the inhibitor candidate can be contacted with the kinase SPR array before the signal-inducing KBM. In such an embodiment, changes in the SPR signal can be measured through the displacement of the inhibitor candidate by the signal-inducing KBM.

In some cases, it may be useful to compare the results of the inhibitor/SG-L-KBM assay to either an ATP/signal-inducing KBM assay or a known kinase inhibitor/signal-inducing KBM assay. The comparative assays can be run, for example, simultaneously in a parallel channel on a different spot of the microarray or can be run before the candidate inhibitor/signal-inducing KBM assay and stored in a computer memory. The results of the candidate inhibitor/signal-inducing KBM assay and the comparative assays can be compared to identify potential inhibitors (e.g., drug candidates). If the comparative assays are run first, they can be run in the same channel/same spot or different channel/different spot than the subsequent candidate inhibitor/signal-inducing KBM assay. Competitive assays also may be useful and would involve inhibitor-ATP/signal-inducing KBM assays or inhibitor-known inhibitor/signal-inducing KBM assays.

Figure 2:
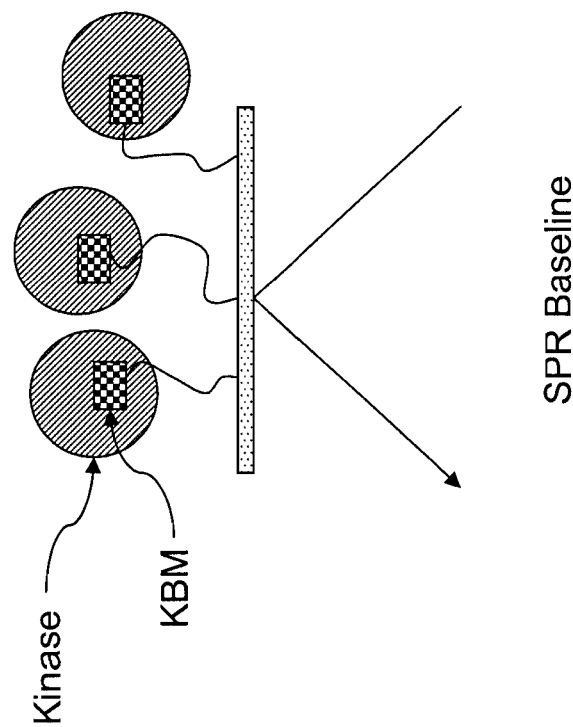
FIG. 2 illustrates a second embodiment of a displacement assay.
Figure 2:
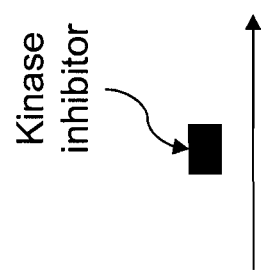
Figure 2:
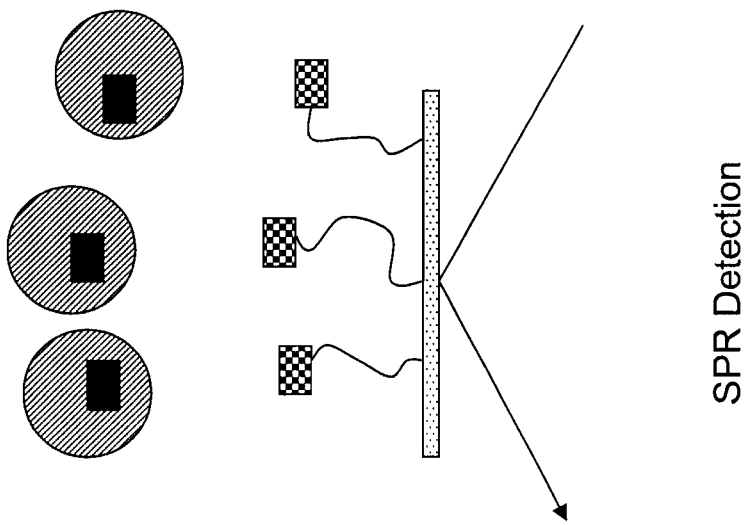
Figure 3:
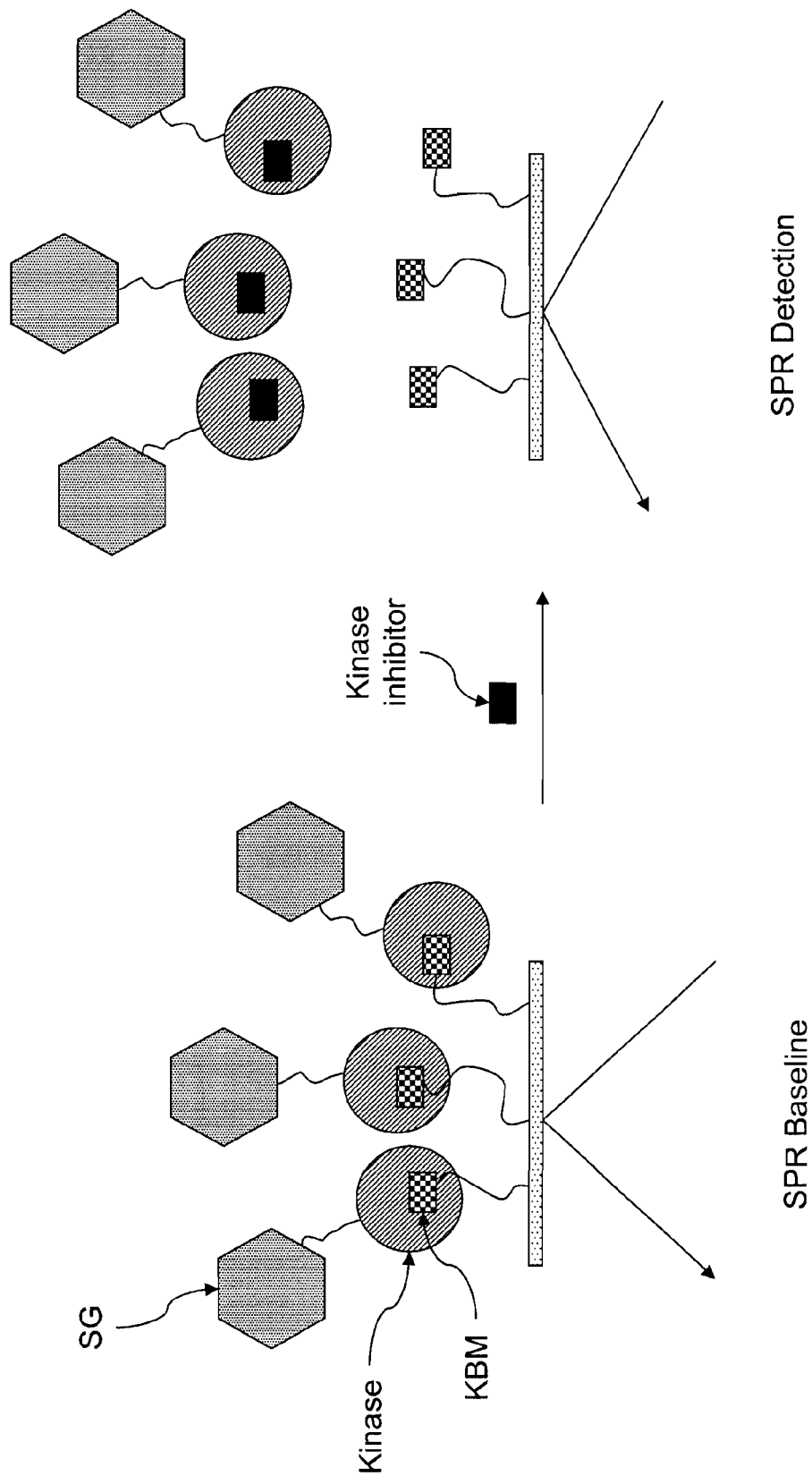
FIG. 3 illustrates a third embodiment of a displacement assay.
Like reference symbols in the various drawings indicate like elements.

Another variation includes a displacement assay in which a KBM is immobilized on the surface, a kinase is loaded and thereby immobilized on the surface through binding to the KBM, an SPR signal is recorded, an unknown inhibitor introduced, and a change in the SPR signal indicates that the kinase has been displaced (e.g., that the unknown binder/inhibitor has comparable or greater affinity for the kinase than the immobilized KBM) (see FIG. 2). The KBM can be immobilized on the surface using chemistries such as those described above for conjugating a KBM to an SG. In these cases, PEG linkers are particularly useful to extend the KBM or known inhibitor into the analyte solution and prevent deleterious interactions of the protein with the surface. The kinase also can be labeled with an SG to amplify the SPR signal prior to displacement (see FIG. 3).

In another embodiment, the disclosure provides for the differentiation between in-ATP-pocket binding versus allosteric or out-of-ATP pocket binding of a molecule (e.g., a protein kinase inhibitor molecule). In one embodiment, an assay comprises introducing an analyte (e.g., a kinase inhibitor drug candidate) to a kinase array loaded with signal-inducing KBMs, which are capable of binding in the ATP binding domain, and measuring binding using SPR. Detection of the displacement of the SG-L-KBM would indicate in-ATP-pocket binding of the protein kinase inhibitor drug candidate, whereas a detection of the non-displacement of the SG-L-KBM in conjunction with the detection of binding of the protein kinase inhibitor drug would indicate allosteric or out-of-ATP-pocket binding.

Also provided herein is a method for validating the functionality of immobilized protein kinases. One current shortcoming of protein arrays is the inability to determine if the arrayed protein is representative structurally and functionally of the protein in vivo. By determining if a signal-inducing KBM, which is known to bind in the ATP binding domain, binds to the individual arrayed protein kinases, a validation of the relevant functionality of the protein kinase can be observed, that is, the presence of a functional ATP binding pocket can be demonstrated.

A number of embodiments of the invention have been described. Nevertheless, it will be understood that various modifications may be made without departing from the spirit and scope of the invention. Accordingly, other embodiments are within the scope of the following claims.

What is claimed is:

1. A method for characterizing a kinase inhibitor candidate using Surface Plasmon Resonance (SPR), comprising:
   a) providing a kinase inhibitor candidate;
   b) providing a compound of the formula:

$[SG]_m$-$[L]_n$-$[KBM]$, wherein SG is a signal inducing group; L is a linker; KBM is a kinase binding molecule; m is an integer from 1 to 5; and n is an integer from 0 to 5;
   c) providing an immobilized kinase SPR array;
   d) contacting the kinase inhibitor candidate and the compound with the immobilized kinase SPR array;

e) measuring the SPR signal of one or both the compound and the kinase inhibitor candidate with the immobilized kinase SPR array; and f) monitoring a change in the SPR signal upon binding or release of the compound or the kinase inhibitor candidate with the immobilized kinase SPR array, thereby characterizing the kinase inhibitor.

2. The method of claim 1, wherein the kinase inhibitor candidate is contacted with the immobilized kinase SPR array after the compound is contacted with the immobilized kinase SPR array.

3. The method of claim 1, wherein the kinase inhibitor candidate is contacted with the immobilized kinase SPR array before the compound is contacted with the immobilized kinase SPR array.

4. The method of claim 1, wherein the kinase inhibitor candidate and the compound are substantially simultaneously contacted with the immobilized kinase SPR array.

5. The method of claim 1, wherein the compound is bound to the immobilized kinase SPR array.

6. The method of claim 1, wherein the kinase inhibitor candidate is bound to the immobilized kinase SPR array.

7. The method of claim 1, further comprising providing a known kinase inhibitor to characterize the kinase inhibitor candidate.

8. The method of claim 7, wherein the known kinase inhibitor is bound to the immobilized kinase SPR array.

9. The method of claim 1, wherein the compound is bound to a binding domain of the kinase in one or more locations on the immobilized kinase SPR array.

10. The method of claim 1, wherein the kinase inhibitor candidate is bound to a binding domain of the kinase in one or more locations on the immobilized kinase SPR array.

11. The method of claim 1, further comprising providing a known kinase inhibitor to characterize the kinase inhibitor candidate in one or more locations on the immobilized kinase SPR array.

12. The method of claim 11, wherein the known kinase inhibitor is bound to a binding domain of the kinase in one or more locations on the immobilized kinase SPR array.

* * * * *

SEQUENCE LISTING

```
<160> NUMBER OF SEQ ID NOS: 6

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Phe Ala Arg Lys Gly Ala Leu Arg Gln Lys Asn Val His Glu Val
1               5                   10                  15
```

Lys Asn

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Phe Ala Arg Lys Gly Ala Leu Arg Gln Lys Asn Val
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Ala Arg Lys Gly Ala Leu Arg Gln
 1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Arg Arg Gly Ala Arg Arg Trp Arg Lys
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Lys Lys Leu Pro Ala Thr Gly Asp
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asn Met Ser Pro Val Gly Asp
 1               5